(12) United States Patent
Wiederhold

(10) Patent No.: US 7,666,620 B2
(45) Date of Patent: Feb. 23, 2010

(54) RAPID TISSUE PROCESSING SYSTEM

(75) Inventor: J. Gary Wiederhold, Plainwell, MI (US)

(73) Assignee: Richard-Allan Scientific Company, Kalamazoo, MI (US)

( * ) Notice: Subject to any disclaimer, the term of this patent is extended or adjusted under 35 U.S.C. 154(b) by 0 days.

(21) Appl. No.: 11/557,531

(22) Filed: Nov. 8, 2006

(65) Prior Publication Data

US 2008/0108043 A1    May 8, 2008

(51) Int. Cl.
    *G01N 1/30* (2006.01)
(52) U.S. Cl. ....................................... 435/40.5
(58) Field of Classification Search ........................ None
    See application file for complete search history.

(56) References Cited

U.S. PATENT DOCUMENTS

| | | | |
|---|---|---|---|
| 4,656,047 A | 4/1987 | Kok et al. | |
| 4,839,194 A | 6/1989 | Malluche et al. | |
| 4,891,239 A | 1/1990 | Dudley et al. | |
| 4,911,915 A | 3/1990 | Fredenburgh | |
| 5,679,333 A | 10/1997 | Dunphy | |
| 5,830,352 A * | 11/1998 | Holm | 210/198.1 |
| 6,017,725 A * | 1/2000 | Hoffmann et al. | 435/40.5 |
| 6,042,874 A | 3/2000 | Visinoni et al. | |
| 6,207,408 B1 * | 3/2001 | Essenfeld et al. | 435/40.5 |
| 6,586,713 B2 | 7/2003 | Essenfeld et al. | |
| 6,902,928 B2 | 6/2005 | Izvoztchikov et al. | |
| 2005/0124028 A1 * | 6/2005 | Windeyer et al. | 435/40.5 |
| 2005/0255540 A1 | 11/2005 | Fredenburgh et al. | |

OTHER PUBLICATIONS

Pollard et al., The Journal of Histochemistry and Ctytochemistry, 1987, vol. 35, No. 11, pp. 1329-1338.*
Werner et al., The American Journal of Surgical Pathology, 2000, vol. 24, No. 7, p. 1016-1019.*
Werner et al., The American Journal of Surgical Pathology, 2000, vol. 24, No. 7, p. 1016-1019.*

* cited by examiner

*Primary Examiner*—L Blaine Lankford
*Assistant Examiner*—Kade Ariani
(74) *Attorney, Agent, or Firm*—Thompson Hine LLP

(57) ABSTRACT

A method for processing a biological tissue specimen using either manual or automated processing. The tissue specimen is sequentially contacted with components of a reagent system in the presence of increased temperature and/or agitation and in the absence of exogenous microwave radiation to facilitate processing in less than one working day.

13 Claims, No Drawings

RAPID TISSUE PROCESSING SYSTEM

BACKGROUND

Traditional histology methods for preserving tissues for microscopy or other forms of examination generally require days to complete. Tissue processing typically involves at least the following steps: (i) fixation, (ii) dehydration, (iii) clearing, and (iv) infiltration with embedding medium. Rapid tissue processing methods utilizing microwave energy were introduced in the late 1980's, for example, as taught in U.S. Pat. No. 4,656,047 to Kok et al., U.S. Pat. No. 4,839,194 to Malluche et al. and U.S. Pat. No. 4,891,239 to Dudley et al. Instruments for performing automated microwave processing are taught in U.S. Pat. No. 4,891,239 and U.S. Pat. No. 6,207,408, among others. Such instruments have been made commercially available and the practice of rapid tissue processing methods is increasing.

Some of the procedures for rapid processing combine steps, for example, simultaneous fixation and dehydration, as taught in U.S. Pat. No. 6,207,408 or simultaneous dehydration and clearing, as described in U.S. Pat. No. 6,042,874. Rapid processing methods utilizing microwave radiation are considered to preclude the need for traditional formaldehyde-containing fixation solutions, also called additive fixation solutions. Instead, fixation in these methods uses fixation solutions containing alcohols, ketones, acids, etc., also called non-additive fixation solutions.

Microwave-assisted processing, however, can be associated with artifacts, particularly when combined with non-additive fixation solution. Some automated microwave-based tissue processors limit the maximum thickness of tissue specimens to about 2.5 mm. To date, instruments for performing automated microwave-assisted processing have been expensive. There is thus a need for an affordable rapid tissue processing system capable of preserving tissue specimens up to 5 mm thick and that more closely follows traditional formaldehyde-based (i.e., additive) methods.

DETAILED DESCRIPTION

A plurality of components, herein described as a processing system, capable of use with commercially available tissue-processing instruments, that utilize an additive-based fixation solution and that utilize warming and agitation to accelerate processing of tissue $\leq 5.0$ mm thick in about five hours or less, and that result in fewer artifacts in the processed tissue. In one embodiment, at least one component in the processing system is warmed during tissue contact to accelerate processing. In one embodiment, at least one component contacts tissue with agitation, including but not limited to centrifugal agitation, rotational agitation, etc.

One non-limiting example of a commercially available tissue-processing instrument is the STP 420 instrument (Micron International, Waldorf, Germany) described generally in U.S. Pat. No. 6,902,928 to Izvoztchikov et al., expressly incorporated by reference herein in its entirety. The reagent system may be used with this instrument, with other instruments, and/or with manual procedures. It will be appreciated by one skilled in the art that processing times using the disclosed processing system may vary, e.g., depending upon differences in temperature and/or agitation force. However, the disclosed processing system achieves tissue processing through steps of tissue holding, fixation, dehydration, clearing, and infiltration in less than one working day (e.g., less than about eight hours). In one embodiment, it achieves tissue processing through these steps in about five hours or less.

At least the following components comprise the processing system: a fixation solution, a dehydration solution, and a clearing solution. Optional components are a holding solution, and an infiltration solution. In one embodiment, the processing system additionally includes a holding solution. In one embodiment, the processing system additionally includes an infiltration solution. It will be appreciated by one skilled in the art that reagents in addition to those in each of the fixation, dehydration, clearing solutions, and optional holding and infiltration solutions, such as buffers or other solutions, may be included in some embodiments. The term solution is used herein in a non-limiting manner to encompass any mixture of components that is or is rendered a liquid.

Holding Solution

The optional holding solution contains formaldehyde. It is used for holding a tissue specimen during transport from site of collection (e.g., grossing station, surgical suite, etc.) to a processing area. In one embodiment, the holding solution contains additional reagents that enhance formaldehyde penetration into the tissue. Examples of such penetrating-enhancing reagents include, but are not limited to, non-ionic detergents such as Triton-X 100, Tween 20, Nonidet-P40, etc., and/or aprotic solvents such as dimethyl sulfoxide (DMSO), and/or other reagents that increase cell membrane permeability. Examples of each of these reagents are known to one skilled in the art.

Tissue specimens up to 5 mm thick are maintained in the holding solution for a minimum of about 20 minutes at ambient temperature (i.e., about 20° C. to about 22° C.). Such tissue specimens may remain in the holding solution longer than 20 minutes, even up to several days.

Fixation Solution

The fixation solution contains formalin that is buffered to a substantially neutral pH. In one embodiment, the fixation solution is buffered from about pH 6.8 to about pH 7.2. The fixation solution also contains reagent grade alcohol that is at least about 95% (v/v) ethanol. In one embodiment, the alcohol component is a mixture of 95% ethanol, 5% (v/v) methanol, 5% (v/v) isopropanol. The fixation solution may contain other components. As one example, the fixation solution may contain DMSO to enhance penetration rate of the fixation solution into tissues. As another example, the fixation solution may contain a polyethylene glycol (PEG), such as PEG 400, that may fill the intracellular spaces as water is removed from cells by exposure to the alcohol component.

In one embodiment, the fixation solution is provided during an automated tissue processing procedure. For example, using the previously described STP 420 instrument, contact between the fixation solution and the tissue specimen at a temperature of 55° C. to 57° C. accelerates fixation without creating significant heat-related artifacts. Concomitant with or in place of heating, agitation provided during fixation further increases penetration rate of the fixation solution into tissues. If using the STP 420 instrument, centrifugal agitation at a medium setting, which is about 12 rpm, is sufficient. Tissue specimens typically remain in the fixation solution for at least about 17 min, or longer as needed. For example, thicker tissue specimens, tissue specimens with a relatively high lipid content, and/or fibrous tissue specimens require longer fixation. Other examples are known to one skilled in the art.

Tissue specimens up to 3 mm thick are usually adequately fixed within about 20 min to about 25 min. Tissue specimens up to 4 mm thick are usually adequately fixed within about 25 min to about 30 min. Tissue specimens up to 5 mm thick are usually adequately fixed within about 35 to about 40 minutes, if previously exposed to a holding solution for at least about 20 minutes. Times may be adjusted as needed, as known to one skilled in the art.

In one embodiment, formalin in the fixation solution is buffered without using salts that are insoluble in alcohol. Phosphate is one example of such a salt, thus, in this embodiment formalin is buffered without using a phosphate buffer. This avoids the need to rinse tissues with warm water following buffered formaldehyde-containing fixation solutions. One example of such a phosphate-free neutral-buffered formalin solution is taught in U.S. patent application Ser. No. 10/845,806, incorporated by reference herein in its entirety. This application discloses maleic acid and maleic acid dipotassium salt for use with formalin-containing fixation solutions, and may be used in the present fixation solution.

Dehydration Solution

After fixation and automated or manual removal of the fixation solution, the fixed tissue specimens are exposing to a dehydration solution. The dehydration solution contains about 90% (v/v) isopropanol and about 9% (v/v) methanol. In one embodiment, the dehydration solution also contains about 0.5% (v/v) formaldehyde. In one embodiment, the dehydration solution also contains about 0.1% (v/v) PEG and about 0.4% (v/v) DMSO. In contrast to these inventive embodiments, a mixture of isopropanol (55% to 70%) and methanol (30% to 45%) is taught in U.S. Pat. No. 4,911,915, incorporated by reference herein in its entirety.

Using the previously described STP 420 instrument, contact between the dehydration solution and the tissue specimen at a temperature of 55° C. to 57° C. accelerates dehydration. Concomitant with or in place of heating, agitation provided during dehydration further increases penetration rate of the dehydration solution into tissues. Tissue specimens typically remain in the dehydration solution for at least about 43 min, or longer as needed. For example, thicker tissue specimens, tissue specimens with a relatively high lipid content, and/or fibrous tissue specimens require longer dehydration. Other examples are known to one skilled in the art.

Tissue specimens up to 3 mm thick are usually adequately dehydrated within about 43 min to about 50 min. Tissue specimens up to 4 mm thick are usually adequately dehydrated within about 128 min to about 135 min. Tissue specimens up to 5 mm thick are usually adequately dehydrated within about 167 to about 175 minutes. Times may be adjusted as needed, as known to one skilled in the art.

Clearing Solution

After tissue specimens are removed from the dehydration solution, they are exposed to a clearing solution that displaces alcohol within the tissue. This alcohol displacement provides for miscibility with paraffin in a subsequent infiltration process. The clearing solution also increases lipid extraction and enhances tissue transparency.

In one embodiment, the clearing solution is xylene based. In one embodiment, the clearing solution is Clear-Rite 3™ based. In one embodiment, a low concentration (e.g., about 1% to about 5%) of an alcohol (e.g., isopropanol) is added to the clearing solution to continue tissue dehydration Using the previously described STP 420 instrument, contact between the clearing solution and the tissue specimen at a temperature of 45° C. to 47° C. accelerates clearing. Concomitant with or in place of heating, agitation provided during clearing further increases penetration rate of the clearing solution into tissues. Tissue specimens typically remain in the clearing solution for at least about 12 min, or longer as needed. For example, thicker tissue specimens, tissue specimens with a relatively high lipid content, and/or fibrous tissue specimens require longer clearing. Other examples are known to one skilled in the art.

Tissue specimens up to 3 mm thick are usually adequately cleared within about 12 min to about 17 min. Tissue specimens up to 4 mm thick are usually adequately cleared within about 15 min to about 20 min. Tissue specimens up to 5 mm thick are usually adequately cleared within about 17 to about 22 min. Times may be adjusted as needed, as known to one skilled in the art.

Infiltration Solution

The optional infiltration solution allows the fixed, dehydrated, and cleared tissue specimen to be infiltrated with melted paraffin, and is generally a final step in preserving tissue specimens.

Using the previously described STP 420 instrument, contact between the infiltration solution and the tissue specimen at a temperature of 62° C. to 64° C. accelerates infiltration. Concomitant with or in place of heating, agitation provided during infiltration further increases penetration rate of the paraffin into tissues. Tissue specimens typically remain in the infiltration solution for at least about 18 min, or longer as needed. For example, thicker tissue specimens, tissue specimens with a relatively high lipid content, and/or fibrous tissue specimens require longer infiltration. Other examples are known to one skilled in the art.

Tissue specimens up to 3 mm thick are usually adequately infiltrated within about 18 min to about 23 min. Tissue specimens up to 4 mm thick are usually adequately infiltrated within about 27 min to about 32 min. Tissue specimens up to 5 mm thick are usually adequately infiltrated within about 45 to about 50 minutes. Times may be adjusted as needed, as known to one skilled in the art.

It will be appreciated that the method and system is applicable for processing any biological tissue specimen, including tissue specimens obtained during surgery, biopsy, and autopsy. Non-limiting examples of tissues include skin, muscle, bowel, breast, heart, kidney, lung, liver, skin, placenta, prostate, pancreas, uterus, bone, brain, stomach, muscle, cartilage, lymph node, adipose tissue, tonsil, gall bladder, spleen, etc. The processed tissue specimen may be stained according to any method, as known to one skilled in the art. Such staining methods include reagents for determination of tissue specimen histopathology, immunopathology, immunocytochemistry, etc.

The invention will be further appreciated with respect to the following Example.

EXAMPLE

A holding solution contained 11% (v/v) formalin buffered to between pH 6.8 to pH 7.2, (formalin comprising about 37% (v/v) formaldehyde in buffered aqueous solution); 69% (v/v) dehydrant comprising at least 95% (v/v) ethanol; 15% (v/v) distilled water; 0.02% (v/v) sodium acetate buffer; 0.5% (v/v) Triton X-100 (non-ionic detergent); and 5% (v/v) DMSO. A specimen from any of bowel, breast, heart, kidney, lung, liver, skin, placenta, prostate, uterus, bone, stomach, muscle, cartilage, lymph node, lipid, tonsil, gall bladder, or spleen tissue was placed into a histology cassette and submerged in the Holding Solution for at least 20 minutes.

The Fixation Solution contained 10% (v/v) formalin; 82% (v/v) reagent grade alcohol (in one embodiment, the alcohol comprised 95% ethanol, 5% methanol, and 5% isopropanol); 2% (v/v) deionized water; 0.02% (v/v) sodium acetate; 1% (v/v) polyethylene glycol (PEG) 400; and 5% (v/v) DMSO. In one embodiment, the Fixation Solution was used as a first step of automated processing with the above described STP 420 instrument. The instrument heated the Fixation Solution to 55° C. to 57° C. and provided centrifugal agitation during contact with the tissue specimen, the duration of which was determined as shown in the following table according to tissue thickness.

The Dehydration Solution is a modification of that disclosed in U.S. Pat. No. 4,911,915, which is expressly incorporated by reference herein. The Dehydration Solution contained 0.5% (v/v) formalin; 90% (v/v) isopropanol; 9% (v/v) methanol; 0.1% (v/v) PEG 400; and 0.4% (v/v) DMSO. The Dehydration Solution was used as a second step of automated processing with the above described STP 420 instrument. The instrument heated the Dehydration Solution to 55° C. to 57° C. and provided centrifugal agitation during contact with the tissue specimen, the duration of which was determined as shown in the following table according to tissue thickness.

The Clearing Solution, in one embodiment, was 95% (v/v) xylene, 5% (v/v) isopropanol. The Clearing Solution, in another embodiment, was 95% (v/v) Clear-Rite 3® (Richard-Allan Scientific, Kalamazoo Mich.), 5% (v/v) isopropanol). The Clearing Solution was used as a third step of automated processing with the above described STP 420 instrument. The instrument heated the Clearing Solution to 45° C. to 47° C. and provided centrifugal agitation during contact with the tissue specimen, the duration of which was determined as shown in the following table according to tissue thickness.

Infiltration, if performed, was the final step of automated processing. The instrument heated the paraffin to melt and maintain it at a temperature between 62° C. to 64° C. In one embodiment, infiltration was facilitated by application of negative pressure (vacuum). In another embodiment, infiltration was facilitated by application of positive pressure.

TABLE

Suggested Minimum Automated Processing Times (minutes)

| Tissue Thickness | Holding Solution | Fixation Solution | Dehydration Solution | Clearing Solution | Infiltration Solution |
|---|---|---|---|---|---|
| ≦3.0 mm | 20-25 | 17-22 | 43-50 | 12-17 | 18-23 |
| ≦4.0 mm | 20-25 | 25-30 | 128-135 | 15-20 | 27-32 |
| ≦5.0 mm | 20-25 | 35-40 | 167-175 | 17-22 | 45-50 |

Complete processing of a tissue specimen (holding, fixation, dehydration, clearing, and infiltration) that was up to about 3.0 mm thick was achieved within 1.5 hours. Complete processing of a tissue specimen that was up about 5 mm thick was achieved in under five hours, making this a same-day procedure.

It should be understood that the embodiments and example described are only illustrative and are not limiting in any way. Therefore, various changes, modifications or alterations to these embodiments may be made or resorted to without departing from the spirit of the invention and the scope of the following claims.

What is claimed is:

1. A method for histologically processing a solid biological tissue specimen for histopathological evaluation, the method comprising,
   (a) contacting a biological tissue specimen equal or <5.0 mm thick with a fixative solution comprising (i) formalin buffered to a substantially neutral pH, and (ii) at least about 95% (v/v) ethanol, at about 55° C. to about 57° C.; then,
   (b) contacting said tissue specimen with a dehydration solution comprising about 90% (v/v) isopropanol and about 9% (v/v) methanol, at about 55° C. to about 57° C.; and then,
   (c) contacting said tissue specimen with a clearing solution,
wherein the processing of said biological tissue specimen equal or <5.0 mm thick in the presence of centrifugal agitation at a temperature not exceeding 57° C. without exposing the tissue specimen to microwave radiation is in less than about five hours.

2. The method of claim 1 wherein the tissue specimen is contacted with a holding solution for at least 20 minutes prior to contact with the fixative solution.

3. The method of claim 2 wherein the tissue specimen is contacted with a holding solution prior to the fixative solution at about 20° to about 22°.

4. The method of claim 1 wherein the tissue specimen is contacted with an infiltrating solution in the presence of centrifugal agitation after the clearing solution at about 62° C. to about 64° C.

5. The method of claim 2 wherein the holding solution comprises a formaldehyde-based solution.

6. The method of claim 4 wherein the infiltrating solution comprises paraffin.

7. The method of claim 2 wherein the holding solution further comprises at least one reagent that facilitates penetration of the fixation solution into the tissue specimen.

8. The method of claim 2 wherein the holding solution further comprises at least one of a non-ionic detergent or an aprotic solvent.

9. The method of claim 8 wherein the non-ionic detergent is selected from the group consisting of Triton-X 100, Tween 20, Nonidet-P40, and combinations thereof.

10. The method of claim 8 wherein the aprotic solvent is dimethyl sulfoxide (DMSO).

11. The method of claim 1 wherein the fixative solution further comprises at least one of polyethylene glycol or DMSO.

12. The method of claim 1 wherein the dehydration solution further comprises about 0.5% (v/v) formaldehyde.

13. The method of claim 1 wherein the dehydration solution further comprises about 0.1% (v/v) PEG and about 0.4% (v/v) DMSO.

* * * * *

UNITED STATES PATENT AND TRADEMARK OFFICE
CERTIFICATE OF CORRECTION

PATENT NO. : 7,666,620 B2
APPLICATION NO. : 11/557531
DATED : February 23, 2010
INVENTOR(S) : J. Gary Wiederhold It is certified that error appears in the above-identified patent and that said Letters Patent is hereby corrected as shown below:

Claim 1(a), Column 6, Line 8: "55° C. to about 57° C." should read --55°C to about 57°C--

Claim 1(b), Column 6, Line 12: "55° C. to about 57° C." should read --55°C to about 57°C--

Claim 1, Column 6, Line 18: "57° C." should read --57°C--

Claim 3, Column 6, Line 26: "20° to about 22°" should read --20°C to about 22°C--

Claim 4, Column 6, Line 29: "62°." should read --62°C--

Signed and Sealed this

Twenty-seventh Day of April, 2010

David J. Kappos
*Director of the United States Patent and Trademark Office*